United States Patent
Greenewald et al.

(10) Patent No.: US 12,238,465 B2
(45) Date of Patent: Feb. 25, 2025

(54) SYSTEMS AND METHODS OF SECURE COMMUNICATION OF DATA FROM MEDICAL DEVICES

(71) Applicant: Physio-Control, Inc., Redmond, WA (US)

(72) Inventors: Robert Greenewald, Snohomish, WA (US); Ryan W. Apperson, Redmond, WA (US); Craig Windish, Kenmore, WA (US); Matthew L Bielstein, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 18/461,696

(22) Filed: Sep. 6, 2023

(65) Prior Publication Data

US 2024/0048874 A1    Feb. 8, 2024

Related U.S. Application Data

(63) Continuation of application No. 17/404,605, filed on Aug. 17, 2021, now Pat. No. 11,792,554, which is a
(Continued)

(51) Int. Cl.
*H04Q 9/00*    (2006.01)
*A61B 5/00*    (2006.01)
(Continued)

(52) U.S. Cl.
CPC ............... *H04Q 9/00* (2013.01); *A61B 5/002* (2013.01); *A61B 5/0024* (2013.01);
(Continued)

(58) Field of Classification Search
CPC .. H04Q 9/00; H04Q 2209/40; H04Q 2209/86; H04B 5/0025; A61B 5/002;
(Continued)

(56) References Cited

U.S. PATENT DOCUMENTS 9,882,610 B1    1/2018 Baker et al.
10,492,684 B2   12/2019 Khachaturian et al.
(Continued)

FOREIGN PATENT DOCUMENTS

WO    WO-2016151479 A1 *  9/2016

OTHER PUBLICATIONS

Office Action for U.S. Appl. No. 17/404,605, mailed on Mar. 14, 2023, Robert Greenewald, "Systems and Methods of Secure Communication of Data From Medical Devices", 17 pages.
(Continued)

*Primary Examiner* — Adnan Aziz
(74) *Attorney, Agent, or Firm* — Lee & Hayes, P.C.

(57) ABSTRACT

Disclosed systems and methods include electronic devices attached to a patient or object that transmit data to other devices over a secure communication channel. The devices can track and/or monitor object(s) and/or patient(s) and transmit the tracked and/or monitored data to other electronic devices. Such data can include monitored patient physiological parameter(s) received and/or sensed by the device, for example. A master of the two devices transmits a communication signal to another device that, in response, initiates a secure wireless communication channel, causes one or more modules on the device to be powered, and, when powered, transmits the tracked and/or sensed physiological data over the secure wireless communication channel to the master device. Some example master devices transmit the communication signal with an instruction to the device to activate an onboard power source that later may be disconnected after the tracked and/or physiological data is transmitted.

20 Claims, 7 Drawing Sheets

Related U.S. Application Data continuation of application No. 16/409,664, filed on May 10, 2019, now Pat. No. 11,109,121.

(60) Provisional application No. 62/763,103, filed on May 10, 2018.

(51) Int. Cl.
*G16H 40/67* (2018.01)
*H04B 5/00* (2024.01)
*H04B 5/70* (2024.01)

(52) U.S. Cl.
CPC .......... *A61B 5/6831* (2013.01); *A61B 5/6833* (2013.01); *A61B 5/746* (2013.01); *G16H 40/67* (2018.01); *H04B 5/70* (2024.01); *A61B 2560/0214* (2013.01); *H04Q 2209/40* (2013.01)

(58) Field of Classification Search
CPC ... A61B 5/0024; A61B 5/6831; A61B 5/6833; A61B 5/746; A61B 2560/0214; A61B 5/0015; A61B 2560/0209; A61B 2560/0219; G16H 40/67
See application file for complete search history.

(56) References Cited

U.S. PATENT DOCUMENTS

| | | | |
|---|---|---|---|
| 10,650,299 | B2 | 5/2020 | Bongers |
| 10,667,687 | B2* | 6/2020 | Lane .................. G16H 40/67 |
| 11,147,505 | B1* | 10/2021 | Shoeb .................. A61B 5/6801 |
| 2004/0113771 | A1* | 6/2004 | Ozaki .................. A61B 5/0002 340/539.12 |
| 2005/0154271 | A1* | 7/2005 | Rasdal .................. G16H 10/60 424/9.1 |
| 2009/0054737 | A1 | 2/2009 | Magar et al. |
| 2009/0076336 | A1 | 3/2009 | Mazar et al. |
| 2010/0198034 | A1 | 8/2010 | Thomas et al. |
| 2011/0019824 | A1 | 1/2011 | Sattiraju et al. |
| 2011/0213225 | A1 | 9/2011 | Bernstein et al. |
| 2011/0275907 | A1 | 11/2011 | Inciardi et al. |
| 2013/0261409 | A1 | 10/2013 | Pathak et al. |
| 2014/0247141 | A1 | 9/2014 | Proud |
| 2014/0266776 | A1 | 9/2014 | Miller et al. |
| 2015/0257647 | A1 | 9/2015 | Buck et al. |
| 2015/0297078 | A1* | 10/2015 | Gross .................. G16H 40/67 340/870.07 |
| 2015/0351674 | A1 | 12/2015 | Thomas et al. |
| 2016/0242685 | A1 | 8/2016 | DeHennis et al. |
| 2016/0270717 | A1* | 9/2016 | Luna .................. A61B 5/743 |
| 2017/0071469 | A1* | 3/2017 | Hijazi .................. A61B 5/0028 |
| 2017/0148297 | A1* | 5/2017 | Ross .................. G08B 21/043 |
| 2017/0182330 | A1 | 6/2017 | Schneider et al. |
| 2017/0249542 | A1 | 8/2017 | Gabriel et al. |
| 2017/0259072 | A1 | 9/2017 | Newham et al. |
| 2017/0325683 | A1 | 11/2017 | Larson et al. |
| 2017/0344736 | A1 | 11/2017 | Lane |
| 2017/0347940 | A1 | 12/2017 | Carr |
| 2018/0026678 | A1 | 1/2018 | Biederman |
| 2018/0139698 | A1 | 5/2018 | Quinlan et al. |
| 2018/0172664 | A1 | 6/2018 | Love et al. |
| 2018/0182491 | A1 | 6/2018 | Belliveau et al. |
| 2018/0228438 | A1 | 8/2018 | Kaskoun et al. |
| 2018/0234133 | A1 | 8/2018 | Biederman |
| 2018/0235468 | A1* | 8/2018 | Khachaturian .... A61B 5/02427 |
| 2019/0015048 | A1 | 1/2019 | Baker |
| 2019/0046038 | A1* | 2/2019 | Weinstein ............ A61B 5/0024 |
| 2019/0363757 | A1 | 11/2019 | Mikolajczak et al. |
| 2021/0169417 | A1* | 6/2021 | Burton ................. A61B 5/4857 |
| 2021/0377632 | A1 | 12/2021 | Greenewald et al. |

OTHER PUBLICATIONS

Non Final Office Action dated Sep. 2, 2020 for U.S. Appl. No. 16/409,664, "Systems and Methods of Secure Communication of Data From Medical Devices", Greenewald, 15 pages.

Office Action for U.S. Appl. No. 16/409,664, mailed on Feb. 3, 2021, Greenewald, "Systems and Methods of Secure Communication of Data From Medical Devices", 29 pages.

Office Action for U.S. Appl. No. 17/404,605, mailed on Sep. 1, 2022, Greenwald, "Systems and Methods of Secure Communication of Data From Medical Devices", 14 pages.

* cited by examiner

SYSTEMS AND METHODS OF SECURE COMMUNICATION OF DATA FROM MEDICAL DEVICES

CROSS-REFERENCE TO RELATED APPLICATION

This application is a continuation of U.S. patent application Ser. No. 17/404,605, filed Aug. 17, 2021, which claims priority to U.S. patent application Ser. No. 16/409,664, filed May 10, 2019, now U.S. Pat. No. 11,109,121 issued Aug. 31, 2021, and which claims priority to U.S. Provisional Patent Application No. 62/763,103 filed May 10, 2018. Application Ser. Nos. 17/404,605, 16/409,664, 62/763,103 and U.S. Pat. No. 11,109,121 are fully incorporated herein by reference.

BACKGROUND

The collection and/or monitoring of physiological data is an important aspect of patient healthcare. Patient physiological data can provide insight into the health and well-being of an individual and provide indication of potential physiological distress. Typically, multiple different medical devices and/or machines are used with each device capturing data regarding a single or sometimes multiple physiological parameters or characteristics. These monitoring systems can be distressing in their own right to the individual connected to the medical device, often causing the individual to experience some level of discomfort.

Additionally, the medical devices can require support for their services, such as connections, like cords or cables, for data transmission and/or power and/or other resources. These connections can limit the mobility and/or use of the medical device as it can be constrained by its support requirements. Constraints, such as these and/or others, can also contribute to the discomfort of the individual due to the decreased range of motion and/or limited movement allowed by the individual while connected to various medical devices and/or monitors.

To assist with the mobility issue, battery operated wireless devices are being adopted to monitor the physiological parameters of a patient. The battery-operated devices have drawbacks, notably the time required to configure the device, the security of the wireless connection used to transmit patient data, and the operating/running time afforded the device by the included batteries. These drawbacks, or constraints, can limit the ability to deploy, or use, such devices.

There exists a need for systems and/or methods that improve the collection and/or monitoring of patients.

DETAILED DESCRIPTION

Figure 1A:
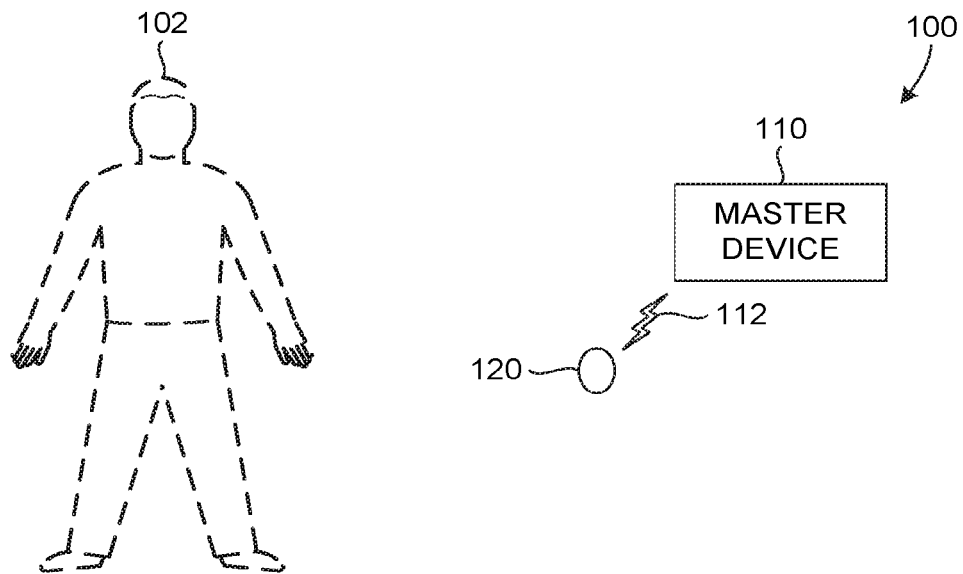
FIGS. 1A-1B illustrate an example near-field communication patch system.

Systems and methods are disclosed here that include devices that communicate with each other over a secure communication channel. Once the secure communication channel is established, devices that track objects and/or monitor data, such as patient physiological parameter data, can transmit that data to another device over the secure communication channel. A master of two devices transmits a communication signal to another device that, in response, initiates the secure wireless communication channel after which the data is transmitted. Some example devices include near field communication (NFC) capabilities that electronically couple the devices using this communication protocol although other communication protocols can also be used. Once the secure communication channel is established, one or more modules in the connected device(s) are powered, either by the initial communication signal itself powering the other device's module(s) or by the initial communication signal instructing an on-device power source to power one or more of the device module(s).

The example embodiments disclosed here describe vital sign patch systems and methods although the same secure communication channel connection can be established between other electronic devices as well. For example, the disclosed vital sign patches can be near-field communication (NFC) patch systems and methods that monitoring patient physiological parameters or track objects to which they are attached. The system, for example, includes a patch having an NFC component and a master device. The patch can be placed on a patient to monitor, sense, collect and/or gather physiological information, or data, regarding one or more physiological parameters of the patient. The patch also includes a communication module to transmit the collected physiological information from the patch to the master device. The patch and the master device can be paired together to activate the patch and to exchange security credentials to establish a secure, wireless communication channel between the patch and master device. The pairing of the patch and master device can include the transmission of an NFC signal from the master device to the patch. Such an NFC signal is a short-range signal requiring the patch to be in physical contact or close proximity to the master device. Typically, most NFC signals operate within a range of 2-4 centimeters (cm) from the master device but can vary in some circumstances.

Receiving the NFC signal induces a current in the patch causing a switch of the patch to complete one or more circuits of the patch to connect an onboard energy source, such as a battery, to one or more components/systems of the patch via the one or more circuits. The one or more circuits can include circuits to provide power to the communication module to transmit the collected physiological information using a communication protocol, such as Wi-Fi, WiGig, and/or Bluetooth®, and circuits to provide power to a physiological monitoring module that includes one or more sensors to sense/collect the physiological information. Collection and/or transmission of the physiological data by/from the patch can be in a continuous or intermittent manner. Additionally, the master device can display/output the collected physiological information and/or can transmit the collected physiological information, or portion thereof, to another device/system, such as for patient monitoring and/or treatment. Further, the patch can be optionally returned to a pre-activated, or dormant, state by a further NFC signal that can cause the switch of the patch to disconnect the onboard energy source from the one or more circuits.

The master device can be a self-contained device, a connectable device, or integrated in another device. As a self-contained device, the master device can be portable allowing it to be carried by a patient to allow for extended monitoring of one or more physiological parameters of the patient. As a connectable device, the master device can be an object that can be connected to another object to provide the functionality/features of the master device. In an example, the master device can be a computer accessory that can be connected to a computer or another medical device to allow the connected device to receive the collected physiological information. As an integrated device, the master device features/functionality can be implemented as software that can utilize the hardware/components of the integrated device to perform the various features/functions of the master device. For example, the master device can be a mobile device with an application installed thereon. The application can use existing hardware of the mobile device, such as the NFC capability and/or communication capability, to pair/activate the patch and to receive physiological, or other, information from the patch.

In another embodiment, the patch can be placed on an object, such as a pill bottle or injectable medication, and can store an identification and/or other information regarding the object. The master device and patch can be paired to cause the patch to transmit the stored identification and/or other information regarding the object upon which the patch is placed. The master device can receive the object identification and can transmit the identification to another device/system and/or can correlate the identification, such as to confirm the proper identification of the object. In this manner, the object can be tracked/monitored using the patch and master device. Additionally, the master device can transmit information to the patch that can be stored by the patch and can be transmitted by the patch later.

The NFC patch system can be deployed in hospital, residential and/or other environments, such as emergency or mass-casualty situations. The ease and efficiency of pairing the NFC patch to a master device allow for the quick application of NFC patches, such as to multiple patients, to monitor one or more patient physiological parameters of one or multiple patients. Further, pairing the NFC patch with the master device in the disclosed manners can help eliminate the risk of pairing it to the incorrect monitor or other master device, which increases accuracy and speed of rescuers in urgent, high-stress environments when patients are suffering medical emergencies. Additionally, a patient can apply the patch and gather physiological monitoring data themselves. The NFC patch can be sufficiently small in size and/or flexible in nature, so as not to unduly inhibit the activities of the patient. The NFC patch can also include environmental protection, such as water resistance/proofing, allowing the NFC patch to be continuously worn by the patient for extended periods of time without undue inconvenience to the patient. Since the NFC patches are in a dormant state prior to activation, the shelf life of the NFC patches is extended with minimal concern of onboard energy source depletion prior to activation. This can allow the NFC patches to be stored and used as needed and/or widely distributed across one or more environments in preparation for use. Further, the master device can be an existing device, or a relatively small device that can be carried by, or transported with, the patient to allow for the continued physiological parameter monitoring as the patient moves/is moved.

Still further, the disclosed devices, can also be included in wearables and/or other articles that are attached to a patient, such as wrist watches, bracelets, harnesses, vests, sleeves, fitted articles of apparel, and any other wearable item(s) and/or article(s). The disclosed examples discussed herein relate to the device in the form of a patch to be placed on a patient and/or object, but equally apply to these alternative wearables embodiments as well.

For example, in a wearables embodiment, a wearer could wear a watch or other article of manufacture or apparel that can operate in multiple states. A first state of the wearable could be the typical function of the article, such as, in the watch example, the wearable would operate as a watch to give the user the time, date, and other related information, and could also track and/or monitor various data about the wearer. The wearable, or watch in this example, could then be switched to a second state of operation in which the wearable would transmit the monitored and/or tracked data about the wearer to a remote device and/or network. For example, the wearable could sense the patient's pulse, blood pressure, heart rate, electrocardiogram (ECG), and/or other sensed data and when activated to the second state, could transmit that data to a remote medical caregiver. The remote medical caregiver can then monitor, instruct on therapy to administer to the patient, deliver therapy (such as defibrillation therapy if the wearable has such a capability), interact in bi-directional communication with a rescuer if the wearer is experiencing a medical emergency, interact in bi-directional communication with the wearer as needed, send uni-directional prompts or instructions to the wearer or a rescuer, etc. The sensed or otherwise tracked data could be transmitted to a remote device or network, as explained in the vital signs patch examples below.

The instruction to switch from the first to the second state of operation could be automatic upon detection or identification of a particular sensed parameter, such as a physiological parameter that is outside a tolerated range of values, for example. Alternatively or additionally, the instruction could be received by the wearable from a remote computing device and/or network to begin transmitting the tracked and/or sensed data. For example, a remote caregiver could periodically check the wearer's tracked and/or monitored physiological parameter data and give treatment and/or therapy advice in response, either immediately upon receipt and review of the data or later on during ongoing treatment of the patient. In another alternative or additional feature, a remote device or network could send an instruction to the wearable to transmit the tracked and/or monitored data according to a preset schedule that may also be customized to the wearer's medical condition or according to previously received data from the patient.

For example, the remote device could be a local monitor defibrillator being used to monitor and/or treat the patient or a remote computing system with a medical caregiver or a patient report system that create a patient report to transmit to the next caregiver along the continuum of care. For example, sensed physiological data and/or therapy delivered to the wearer by a rescuer or the wearable could be included in a patient report that is sent to the hospital caregiver team while the wearer is being transported to the hospital from the site of an emergency event.

Figure 1B:
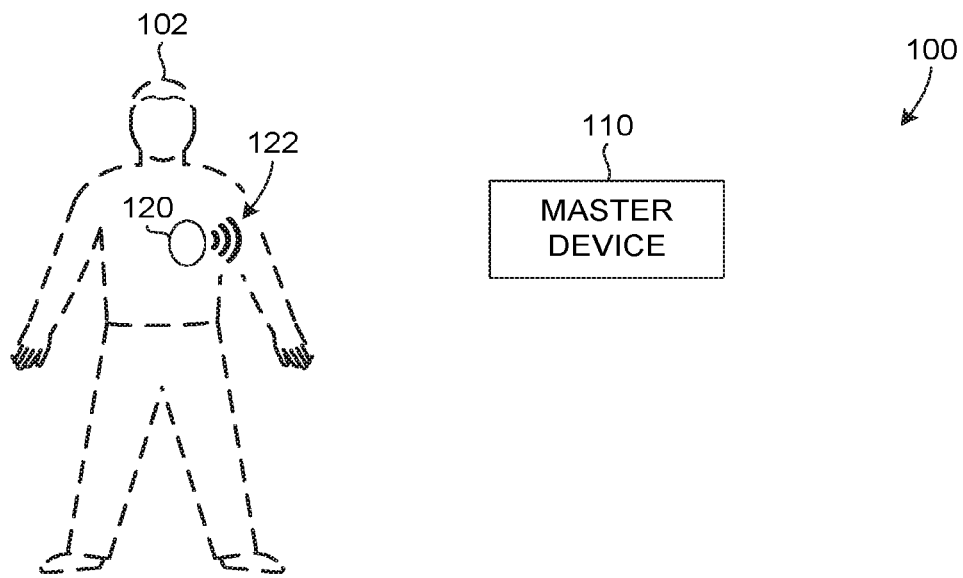

FIGS. 1A and 1B illustrate an example near-field communication (NFC) patch system 100. FIG. 1A illustrates an NFC patch 120 being prepared to be placed on a patient 102.

The NFC patch 120 can include sensors to monitor one or more physiological signs of the patient 102 and can transmit data gathered by the monitoring to an external device.

To prepare, or activate, the NFC patch 120, the NFC patch 120 can be brought into the proximity of a master device 110 that can emit an NFC signal 112. Emission of the NFC signal 112 can be a constant or selective. Selectively emitting the NFC signal 112 can be caused by a user, device and/or system triggering the master device 110 to emit the NFC signal. Alternatively, the emission of the NFC signal 112 can be triggered by detecting the NFC patch 120 being within the proximity of the master device 110. The NFC signal 112 can be a radio frequency (RF) signal that can be received by the NFC patch 120. Reception of the NFC signal 112 by the NFC patch 120 can induce a current in the NFC patch 120 that can power one or more circuits and/or elements of the NFC patch 120 to activate the patch 120.

Activation of the NFC patch 120 can cause an onboard energy source, such as a battery to be activated by connecting the energy source to one or more circuits and/or elements of the NFC patch 120. The onboard energy source can be connected to a monitoring circuit of the NFC patch 120 that includes a sensor for monitoring the one or more physiological parameters. Additionally, upon activation, the NFC patch 120 can transmit a pairing, or other, code to the master device 110 to establish a wireless communication channel between the NFC patch 120 and the master device 110. The established communication channel can be secured, using the pairing, or other, code as authentication/synchronization between the NFC patch 12 and the master device 110. Alternatively, the wireless communication channel can be insecure. Various communication protocols, such as Wi-Fi, WiGig, and/or Bluetooth®, can be used to establish a secure, wireless communication channel between the NFC patch 120 and the master device 110. The secure, wireless communication channel can be unique to the NFC patch 120 and master device 110 pair. The master device 110 can optionally support the ability to pair to multiple NFC patches 120. For example, two or more NFC patches 120 can be paired with the master device 110 to communicate via individual secure, wireless communication channels. Alternatively, a single secure, or other, wireless communication channel can exist between the two or more NFC patches 120 and the master device 110.

Since the onboard energy source of the NFC patch 120 is only connected/activated upon activation of the NFC patch 120, the onboard energy source is not, or is minimally, drained or depleted while the NFC patch 120 is in a dormant state. This can allow the NFC patch 120 to be stored/unused for a period of time, i.e. a long shelf life. Further, activation of the NFC patch 120 via the NFC signal 110, rather than a button or physical actuation, can prevent the NFC patch 120 from being inadvertently being activated during handling. Inadvertent activation of the NFC patch 120 can cause draining/depletion of the onboard energy source while the NFC patch 120 is not in use, which can reduce the usability of the NFC patch 120 in an active, physiological monitoring state.

Once activated and paired with the master device 110, the NFC patch 120 can be placed on the patient 102 to monitor the one or more physiological parameters. FIG. 1B illustrates the NFC patch 120 in place on the patient 102. The NFC patch 120 can monitor the one or more physiological parameters and can transmit collected data, such as data indicative of the monitored/measured physiological parameter(s), to the master device 110 via the secure, wireless communication channel 122. The monitoring of the one or more physiological parameters and/or the transmission of the collected data can be continuous, allowing for real-time monitoring and transmission of physiological parameter data, or it can be intermittent, such as according to a schedule and/or a trigger. For example, the NFC patch 120 can include a circuit and/or element that can trigger, or cause, the collection and/or transmission of physiological parameter data at regular intervals. The regular interval can be predetermined and/or can be configurable, such as by the master device 110 via the NFC signal 112 and/or the secure, wireless communication channel 122. Alternatively, the NFC signal 112 can be intermittently emitted by the master device 110 to cause the collection and/or transmission of physiological parameter data by the NFC patch 120.

To terminate the collection and/or transmission of physiological, or other, data from the NFC patch 120 to the master device 110, the NFC signal 112, the wireless communication channel 122, or other signal, can be emitted by the master device 110 to trigger, or cause, the NFC patch 120 to disengage the onboard energy source. Disengaging the onboard energy source from the one or more previously connected circuits and/or elements can cause the NFC patch 120 to return to a dormant state. The pairing/activation process of FIG. 1A can be performed again to reactivate and use the NFC patch 120.

The NFC patch 120 can be a disposable item, such as for a single-use and/or for use with a single patient 102. The cost of components and/or manufacture of the NFC patch 120 can be sufficiently low to allow for the economic and/or efficient use of the NFC patch 120 in a disposable manner. The disposability of the NFC patch 120 can also assist with patient 102 safety, by allowing the NFC patch 120 to be single patient use, which helps prevent the spread of infection that can occur with cleaning and sterilizing medical equipment for re-use, for example. Alternatively, the NFC patch 120 can be reusable to allow the NFC patch 120 to be used multiple times with one or more patients 102. The reusable NFC patch 120 can be constructed to allow it to be sufficiently clean between uses and/or patients, such as waterproof, ability to be sterilized and/or other properties/characteristics to allow the NFC patch 120 to undergo one or more cleaning/disinfecting, or other, processes.

The NFC patch 120 can also be modular to allow one or more elements/components of the NFC patch 120 to be removed and/or replaced. For example, the sensor portion of the NFC patch 120 can be configurable/modular, to allow a user to select and place a selected sensor portion on the NFC patch 120 for use. Other modular/replaceable elements/components can include the onboard energy source that can be replaceable when depleted. Alternatively, the NFC patch 120 can be a single item with the elements/components permanently affixed and/or sealed thereto.

Figure 2:
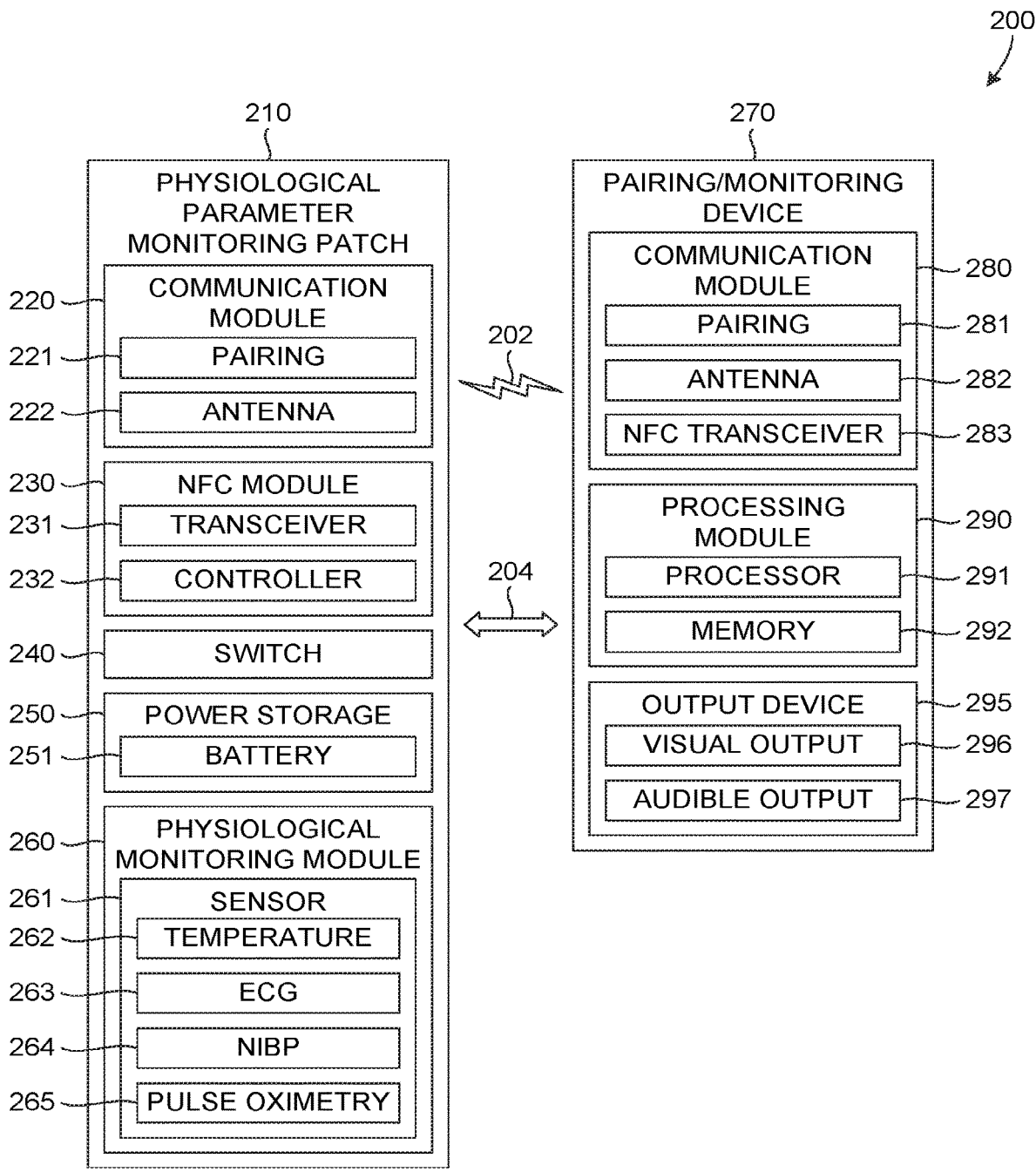
FIG. 2 illustrates an example block diagram of a near-field communication patch system.

FIG. 2 is a block diagram of an example near-field communication (NFC) patch system 200 that includes a physiological parameter monitoring patch 210 and a pairing/monitoring device 270. The physiological parameter monitoring patch 210 can be in a dormant state until activated by an NFC signal, such as 202, from the pairing/monitoring device 270. The NFC signal can be transmitted by the pairing/monitoring device 270 selectively, such as being caused by a user interacting with the pairing/monitoring device 270, automatic, such as by constantly broadcasting the NFC signal, and/or by locating the physiological parameter monitoring patch 210 within a proximity of the pairing/monitoring device 270. In an example, the pairing/monitoring device 270 can constantly broadcast the NFC signal and the physiological parameter monitoring patch 210 can be placed and/or located within the range of the NFC signal and the physiological parameter monitoring patch 210 can establish a communication channel, such as 204, with the pairing/monitoring device 270 in response to receiving the NFC signal. Once the communication channel between the physiological parameter monitoring patch 210 and the pairing/monitoring device 270 is established, the pairing/monitoring device 270 can cease transmission of the automatically broadcasted NFC signal.

In another example, the pairing/monitoring device 270 can broadcast a signal, such as a low power NFC signal, that can be received by the physiological parameter monitoring patch 210 when the physiological parameter monitoring patch 210 and pairing/monitoring device 270 are in near physical proximity of each other. The reception of the low power NFC signal by the physiological parameter monitoring patch 210 can cause the low power NFC signal to draw additional power from the pairing/monitoring device 270. That is the power draw from the pairing/monitoring device 270 to broadcast the low power NFC signal can increase when the low power NFC signal is received by and induces an electric current in the physiological parameter monitoring patch 210. The physiological parameter monitoring patch 210 can be activated by this low power NFC signal and/or the pairing/monitoring device 270 can transmit a higher power NFC signal in response to detecting the increased power draw of the low power NFC signal. The higher power NFC signal transmitted by the pairing/monitoring device 270 can then activate the physiological parameter monitoring patch 210.

The physiological parameter monitoring patch 210 can include a communication module 220, an NFC module 230, a switch 240, power storage 250 and a physiological monitoring module 260. Prior to activation, the physiological parameter monitoring patch 210 can be in a dormant state which can include the disconnection of the power storage 250 from one or more power drawing components of the physiological parameter monitoring patch 210, such as the communication module 220 and/or the physiological monitoring module 260. Reception of an NFC signal, such as from the pairing/monitoring device 270, by the NFC module 230 can cause the physiological parameter monitoring patch 210 to enter an active state in which the communication module and/or the physiological monitoring module 260 are activated and connected to the power storage 250. The physiological monitoring module 260 can begin sensing/collecting physiological parameter data about a patient and one or more of their physiological parameters. The physiological parameter data can then be routed to the communication module 220. The communication module 220 can transmit the sensed/collected physiological parameter data and/or other data from the physiological parameter monitoring patch 210 to the pairing/monitoring device 270 via a communication channel between the two. The NFC module 230 can receive a second NFC signal, that can be the same or different than the initial NFC signal. The reception of the second NFC signal can cause the physiological parameter monitoring patch 210 to return to a dormant state by causing the power storage 250 to be disconnected from the power drawing components of the physiological parameter monitoring patch 210.

The communication module 220 can include a pairing code 221 and an antenna 222. The communication module 220 can communicate with one or more external devices and/or systems, such as the pairing/monitoring device 270, using one or more wireless communication protocols, such as Wi-Fi, WiGig, and/or Bluetooth®. The wireless communication protocol can allow a secured and/or insecure communication channel to be established between the communication module 220 and the external device(s)/system(s). Pairing code 221 can be used as an authentication/synchronization to establish a secure communication channel between the communication module 220 and the external device(s)/system(s). In an example, the pairing code 221 can be a shared secret, such as a link key, that is generated by, and/or stored in, the communication module 220. The pairing code 221 can be shared with the external device/system so that both the communication module 220 and the paired external device/system, such as the pairing/monitoring device 270, both contain the pairing code 221. Authentication and security of the secure communication channel established between the communication module 220 and the external device/system can be confirmed by the shared pairing code 221 of the two devices.

Alternatively, other secure communication channel protocols and/or implementations can be used to establish the secure communication channel between the communication module 220 and an external device/system, such as the pairing/monitoring device 270. In an example, the physiological parameter monitoring patch 210 can include a passcode, such as a predetermined password/passphrase that can be disposed on physiological parameter monitoring patch 210. The predetermined password/passphrase can be entered in the external device/system, such as the pairing/monitoring device, to establish a secure communication channel between the physiological parameter monitoring patch 210 and the external device/system. The password/passphrase can be used to authenticate the external device/system to the communication module 220 to establish the secure communication channel. To enter the predetermined password/passphrase, a user can enter the password/passphrase into the external device/system using an input device. Alternatively, the external device/system can include a capture device that can capture the predetermined password/passphrase and store the captured password/passphrase for authentication to the physiological parameter monitoring patch 210. For example, the external device/system can include a camera that can image a predetermined password/passphrase, such a matrix encoded password/passphrase that is disposed on the physiological parameter monitoring patch 210. The ability for the external device/system to capture and store the predetermined password/passphrase with minimal to no user intervention can increase the efficiency and/or accuracy of transferring the predetermined password/passphrase to the external device/system. The predetermined password/passphrase can be used to authenticate and/or establish a secure communication channel between the physiological parameter monitoring patch 210 and the external device/system.

The antenna 222 can be electrically connected to the communication module 220 to broadcast one or more signals from the communication module 220, such as the transmission of physiological data. The antenna can also receive incoming signals from an external device and/or system, such as the pairing/monitoring device 210. The incoming signals can be processed by the communication module 220 or other component of the physiological parameter monitoring patch 210.

The NFC module 230 can include a transceiver 231 and a controller 232. The transceiver 231 can transmit and receive signals from/to the NFC module 230. For example, the transceiver 231 can receive a signal, such as an NFC signal, from an external device and/or system. The reception of a signal by the NFC module, or the transceiver 231, can induce a current in the NFC module. An antenna, circuitry and/or wiring of the NFC module 230, or transceiver 231, can be arranged and/or constructed to cause a current to be induced in the NFC module 230 by the reception of a signal, such as the NFC signal. The induced current can power one or more components of the NFC module, such as the transmitter capabilities of the transceiver 231 and/or the controller 232.

Alternatively, the controller 232 shown in FIG. 2 could be included in the communication module 220 or could be a standalone component in the physiological parameter monitoring patch 210. Regardless of where the controller physically resides, it can be powered by the induced current of the NFC module 230 to perform one or more functions and/or features of the physiological parameter monitoring patch 210.

In an example, the controller 232 can receive, or retrieve the pairing code 221 from the communication module 220 and can cause the pairing code 221 to be transmitted to an external device/system by the transceiver 231. Additionally, the controller 232 can cause the switch 240 to be activated to connect the power storage 250 to one or more powered components of the physiological parameter monitoring patch 210, such as the communication module 220 and/or the physiological monitoring module 260. In this manner, the controller 232 causes the activation of the physiological parameter monitoring patch 210, by activating the switch 240, and the pairing of the physiological parameter monitoring patch 210 with an external device/system, such as the pairing/monitoring device 270, in response to the received NFC signal. Control of the switch 240 by the NFC module 230 can prevent the inadvertent connection of the power storage 250 to one or more powered components of the physiological parameter monitoring patch 210, which can prevent undue/unnecessary depletion of the power storage 250 prior to use of the physiological parameter monitoring patch 210. Additionally, the controller 232 of the NFC module 230 can also cause the switch 240 to disconnect the power storage 250 from the one or more powered components of the physiological parameter monitoring patch 210 in response to a second received signal, such as another NFC signal. In this manner, the NFC module 230 can control the active and dormant states of the physiological parameter monitoring patch 210 in response to received NFC, or other, signals by controlling the switch 240.

In an embodiment, the NFC module 230 can also harvest power from one or more signals, such as a constantly broadcasted NFC signal, to provide the necessary electrical power to the one or more powered components of the physiological parameter monitoring patch 210. The powered components, such as the communication module 220 and/or the physiological parameter monitoring module 260, can be of a low-power design. The low-power design of the powered components can reduce the amount of energy required to be harvested by the NFC module 230. The reduced energy requirement can allow the NFC module 230 to have a relatively small form factor so that the various components can be fit on the physiological parameter monitoring patch 210.

The switch 240 can be electrically connected to the power storage 250, the NFC module 230 and the powered components of the physiological parameter monitoring patch 210, such as the communication module 220 and/or the physiological monitoring module 260. In response to a signal from the NFC module 230, such as a digital output, the switch 240 can close one or more connections to complete one or more circuits to provide power from the power storage 250 to the powered components of the physiological parameter monitoring patch 210 and/or the NFC module 230. Once connected to the power storage 250, the one or more powered components and/or the NFC module 230 can perform one or more functions, such as the collection and/or transmission of physiological data. In an example, the switch 240 can be a metal-oxide semiconductor field-effect transistor (MOSFET), or other suitable, element that can complete one or more circuits in response to an input, such as a signal from the NFC module 230. The switch 240 can also be a mechanical switch that can be electrically operated by the NFC module 230 and/or manually actuated by a user to prepare and/or active the physiological parameter monitoring patch 210 for use.

The power storage 250 can include a battery 251, or other power/energy storage device, such as any energy harvesting source like solar or thermal power. The power storage 250 can be selectively electrically coupled to one or more other components/systems of the physiological parameter monitoring patch 210, such as in response to a signal from the NFC module 230 to the switch 240. Once electrically connected, the one or more components/systems of the physiological parameter monitoring patch 210 can be supplied electrical power by the battery 251 of the power storage 250. The size, or capacity, of the battery 251 can be sufficient to supply the necessary electrical energy for a desired and/or required runtime, or use time, of the physiological parameter monitoring patch 210. The powered components/systems of the physiological parameter monitoring patch 210, such as the communication module 220 and/or the physiological parameter monitoring module 260, can have various power consumptions based on the communication protocol used and/or the power requirements physiological monitoring module 260 based on the one or more physiological parameters being monitored. For power intensive monitoring, such as the continuous streaming of physiological data from physiological parameter monitoring patch 210 and/or the monitoring of certain physiological parameters, the battery 251 of the physiological parameter monitoring patch 210 can have an increased energy capacity, such as a cylindrical lithium ion cell(s), for example. For monitoring the lower power consumption, the battery 251 can have a lower energy capacity, and likely a smaller form factor due to the decreased energy capacity, such as carbon-zinc or coin cell batteries, for example. Additionally, the battery 251, and/or other energy storage devices of the power storage 250, can be selectively removable to allow the replacement of the battery 251 with a new and/or recharged battery 251 both by physical connection and by wireless/inductive charging.

In an embodiment, the power/energy storage device of the power storage 250 can be a capacitor for some short-use applications like a single use thermometer, for example, and other applications in which limited duration power consumption is required. The capacitor can store and release electrical energy to provide electrical power to the one or more electrically connected components/systems of the physiological parameter monitoring patch 210. The capacitor can be charged by the NFC module 230 receiving one or more signals, such as an NFC signal, that induce a current in the NFC module 230 that can be used to charge the capacitor of the power storage 250.

The physiological monitoring module 260 can include one or more sensors 261 to monitor one or more physiological parameters of a person, such as a patient. The physiological parameter monitoring patch 210 can be activated and placed onto a person, where the physiological parameter monitoring module 260 senses and/or collects physiological data of the one or more physiological parameters being monitored. The sensed/collected physiological data can then be transmitted from the physiological monitoring module 260 to the communication module 220 for transmission to an external device and/or system, such as the pairing/monitoring device 270. Example sensors 261 can include sensors to monitor a temperature 262, an electrocardiogram (ECG) 263, a non-invasive blood pressure (NIBP) 264, a pulse oximetry 265 and/or other sensors to monitor, or collect data on, one or more physiological parameters of a patient. The temperature sensor 262 can include a thermocouple, or other temperature sensing element, to sense data regarding the temperature of the patient on which the physiological parameter monitoring patch 210 is placed. The ECG sensor 263 can include one or more electrodes to monitor and/or collect ECG data of the patient on which the physiological parameter monitoring patch 210 is placed. The NIBP sensor 264 can include one or more elements/systems to collect data regarding the blood pressure of the patient on which the physiological parameter monitoring patch 210 is placed. The pulse oximetry sensor 265 can include a light emitter and detector to determine an oxygen saturation (Sp02) of the patient on which the physiological parameter monitoring patch 210 is placed.

Data regarding the one or more sensed/monitored physiological parameters can be collected continuously or intermittently by the sensor 261. In an example in which the data is collected intermittently, the controller 232 of the NFC module 230, or other control device/system of the physiological parameter monitoring patch 210, can cause the sensor 261 to collect physiological data in an intermittent manner. The intermittent manner can be at regularly occurring intervals, such as predetermined intervals or in response to a regularly received signal from an external device/system, such as from the pairing/monitoring device 270. The intermittent manner can also be selective, such as in response to a received signal from an external device/system, such as from the pairing/monitoring device 270. The selective manner can allow a user to query the physiological parameter monitoring patch 210 as needed, to obtain physiological data. The physiological data can be collected by an analog or digital signal. For applications in which the data is sensed by an analog signal, the data is then converted to a digital signal using an analog to digital converter (ADC).

In addition to collecting physiological data continuously or intermittently by the physiological monitoring module 260, the physiological parameter monitoring patch 210 can continuously or intermittently transmit the collected physiological data, such as by intermittently transmitting the collected data from the communication module 220 and/or by the physiological monitoring module 260 intermittently transmitting the collected physiological data to the communication module 220 for transmission.

Intermittently collecting physiological data and/or transmitting the collected physiological data can allow the power storage 250 to last for a longer overall period of time until depleted beyond a usable level since the power from the power storage 250 is intermittently used. Intermittently collecting physiological data can include collecting physiological data by the physiological monitoring module 260 intermittently for a period of time. For example, the intermittent collection/transmission of physiological data can be at regular intervals, such as every 5 minutes, and the collection interval can be 1 minute. That is, 1 minute of physiological data will be collected and transmitted with a 5-minute pause between the 1-minute collection intervals. Alternatively, the intermittent collection/transmission of physiological data can include the continuous collection of physiological data, such as by the physiological monitoring module 260, and the intermittent transmission of the collected physiological data. For example, every 5 minutes, the collected physiological data, physiological data collected during that 5-minute interval, can be transmitted from the physiological parameter monitoring patch 210, such as by the communication module 220.

The pairing/monitoring device 270 can include a communication module 280, a processing module 290 and an optional output device 295. The communication module 280 can broadcast an NFC signal to and establish a communication channel with the physiological parameter monitoring patch 210 to activate and receive physiological data from the physiological parameter monitoring patch 210. The processing module 290 can control one or more functions and/or features of the pairing/monitoring device 270 and/or can store various data, such as the received physiological data from the physiological parameter monitoring patch 210. The output device 295 can output information, such as indications of pairing with the physiological parameter monitoring patch 210, information regarding the received physiological data from the physiological parameter monitoring patch 210 and/or information regarding one or more functions/features of the pairing/monitoring device 270.

The communication module 280 can include a pairing 281, such as a pairing code, an antenna 282 and an NFC transceiver 283. The pairing 281 can include a code or other cryptographic/authentication item such, as a passcode/passphrase. To pair the pairing/monitoring device 270 and the physiological parameter monitoring patch 210, the pairing 281 can be shared from the pairing/monitoring device 270 or the physiological parameter monitoring patch 210 can share a pairing 221 that can be stored in the pairing/monitoring device 270 as pairing 281. The pairing data is synchronized between the two paired devices, such as the physiological parameter monitoring patch 210 and the pairing/monitoring device 270. The pairing of the two devices allow the devices to authenticate and/or secure communications between the two paired devices.

The communication module 280 can receive information, such as physiological data, from the communication module 220 of the physiological parameter monitoring patch 210 and/or can transmit information to the physiological parameter monitoring patch 210 via the antenna 282. Additionally, or alternatively, the communication module 280 can establish a communication channel with an external device/system, other than the physiological parameter monitoring patch 210, via the antenna 282. In this manner, the collected physiological data received by the communication module from physiological parameter monitoring patch 210 can be transmitted to the external device/system, such as a remote server, a medical device, a nursing station, a visual display and/or other devices/systems.

The NFC transceiver 282 can broadcast the NFC signal from the pairing/monitoring device 270. The NFC signal can be received by the physiological parameter monitoring patch 210 to activate the physiological parameter monitoring patch 210. The NFC transceiver 282 can also receive information and/or data from the NFC module 230 of the physiological parameter monitoring patch 210, such as the pairing 221 of the physiological parameter monitoring patch 210. The received pairing 221 by the NFC transceiver 283 can be stored as pairing 281 of the communication module 280 to establish the communication channel between the physiological parameter monitoring patch 210 and the pairing/ monitoring device 270. The NFC transceiver 282 can selectively, intermittently, or continuously broadcast the NFC signal, the broadcast of which can be terminated upon the pairing of the physiological parameter monitoring patch 210 and the pairing/monitoring device 270.

To pair the physiological parameter monitoring patch 210, a user can "tap" the physiological parameter monitoring patch 210 to the pairing/monitoring device 270 and/or place the physiological parameter monitoring patch 210 within range of the NFC signal from the NFC transceiver 283. The two devices, the physiological parameter monitoring patch 210 and the pairing/monitoring device 270, can exchange pairing information, such as pairing 221 and/or 281, to establish a communication channel between the two devices. The pairing of the physiological parameter monitoring patch 210 and the pairing/monitoring module 270 can therefore be an efficient and/or fast process that requires little user intervention to perform. The reduced user intervention can also reduce the potential for error during the pairing process. The efficiency/speed of the pairing process can allow the NFC patch system 200 to be quickly and/or efficiently deployed in emergency situations, such as mass casualty situations. A user can quickly pair one or more physiological parameter monitoring patches 210 with a pairing/monitoring device 270 that can be assigned to an individual patient. The one or more physiological parameter monitoring patches 210 can provide physiological data for one or more physiological parameters of the patient to the pairing/monitoring device 270. The collected physiological data can then be used to assess, monitor and/or treat the patient.

The NFC transceiver 283 can also broadcast a power signal. The power signal can be received by the physiological parameter monitoring patch 210 to power one or more components, functions and/or features of the physiological parameter monitoring patch 210. In an example, the NFC transceiver 283 can first broadcast the NFC signal to pair the pairing/monitoring device 270 and the physiological parameter monitoring patch 210, once paired, the NFC transceiver 283 can broadcast the power signal to supply power to the physiological parameter monitoring patch 210 by inducing a current in the NFC module 230 of the physiological parameter monitoring patch 210.

The processing module 290 can include a processor 291 and memory 292. The processor 291 can execute one or more instructions, such as instructions stored in the memory 292, to control one or more features of the pairing/monitoring device 270. Controlling one or more features of the pairing/monitoring device 270 by the processor 291, can include controlling the communication with and/or activation of the physiological parameter monitoring patch 210 by the communication module 280 and/or the receiving, processing, analyzing and/or storage of physiological data received from the physiological parameter monitoring patch 210. The physiological data received from the physiological parameter monitoring patch 210 can be stored in the memory 292, as can any processing/analysis of the received physiological data.

The output device 295 can include a visual output 296, such as a display, and/or an audible output 297, such as a speaker. The output device 295 can output the received physiological data from the physiological parameter monitoring patch 210 to convey such data to a nearby user. Additionally, the processing module 290 can perform analysis of the received physiological data, such as an assessment of the data to a normal value or range, and the output module 295 can provide an output based on such analysis. For example, if the pairing/monitoring device 270 determines an abnormal value of a physiological parameter monitored via the physiological parameter monitoring patch 210, the output device 295 can output an alarm or notification to alert a user to the abnormal measurement. The audible output can also be used to alert a user/rescuer that the physiological parameter monitoring patch 210 is activated, paired, and deactivated, among other alerts. The user/rescuer notification can be audible, visual, haptic or some combination thereof.

The pairing/monitoring device 270 can be a self-contained device, a device that can be connected to another device and/or the various functionality/features of the pairing/monitoring device 270 can be integrated with another device. In an embodiment, the pairing monitoring device 270 can be a self-contained device that can be connected to a power source, such as via a cord, can be wirelessly charged by inductive charging, for example, or can include its own power supply, such as a battery. The self-contained, pairing/monitoring device 270 can be portable allowing it to be brought to and/or transported with a patient.

In another embodiment, the paring/monitoring device 270 can be a connectable device, such as computer accessory, that can be connected to one or more devices, such as a computer or medical device, to provide the functionality/features described herein. As a connectable device, the pairing/monitoring device 270 can pair with and receive physiological data from the physiological parameter monitoring patch 210, the received physiological data can then be transmitted to the connected device, such as a computer or medical device. For example, the pairing/monitoring device 270 can be a USB (Universal Serial Bus) dongle that can be connected to a USB port of a computer or medical device to allow the connected device to receive physiological data from the physiological parameter monitoring patch 210.

In a further embodiment, the functionality/features of the pairing/monitoring device 270 can be integrated in another device. The other device can include existing hardware, such as a communication module 280 and an NFC transceiver 283, and the pairing/monitoring device 270 can be software, such as an application, that can utilize hardware functionality of the other device to provide the pairing/monitoring device 270 functionality/features described herein. For example, the pairing/monitoring device 270 can be an application, or app, that can be installed on a mobile device, such as a cellular phone or a tablet computer. The mobile device can include existing hardware that can be utilized by the pairing/monitoring device 270 app to provide/allow the functionality described herein. As a software implementation, the pairing/monitoring device 270 can be installed on existing devices, which can increase the efficiency and/or speed of the NFC monitoring patch system 200. Additionally, such software implementation of the pairing/monitoring device 270 can allow the pairing/monitoring device 270 to integrate with one or more existing programs and/or systems, such as a patient record keeping system. Further, the software implementation can be installed on a patient's mobile device, tablet, smart phone, or any other computing device to allow the continued collection of physiological data via the physiological parameter monitoring patch 210. Collected physiological data can then be transmitted to a healthcare system and/or provider to allow for monitoring and/or treatment of the patient.

Figure 3:
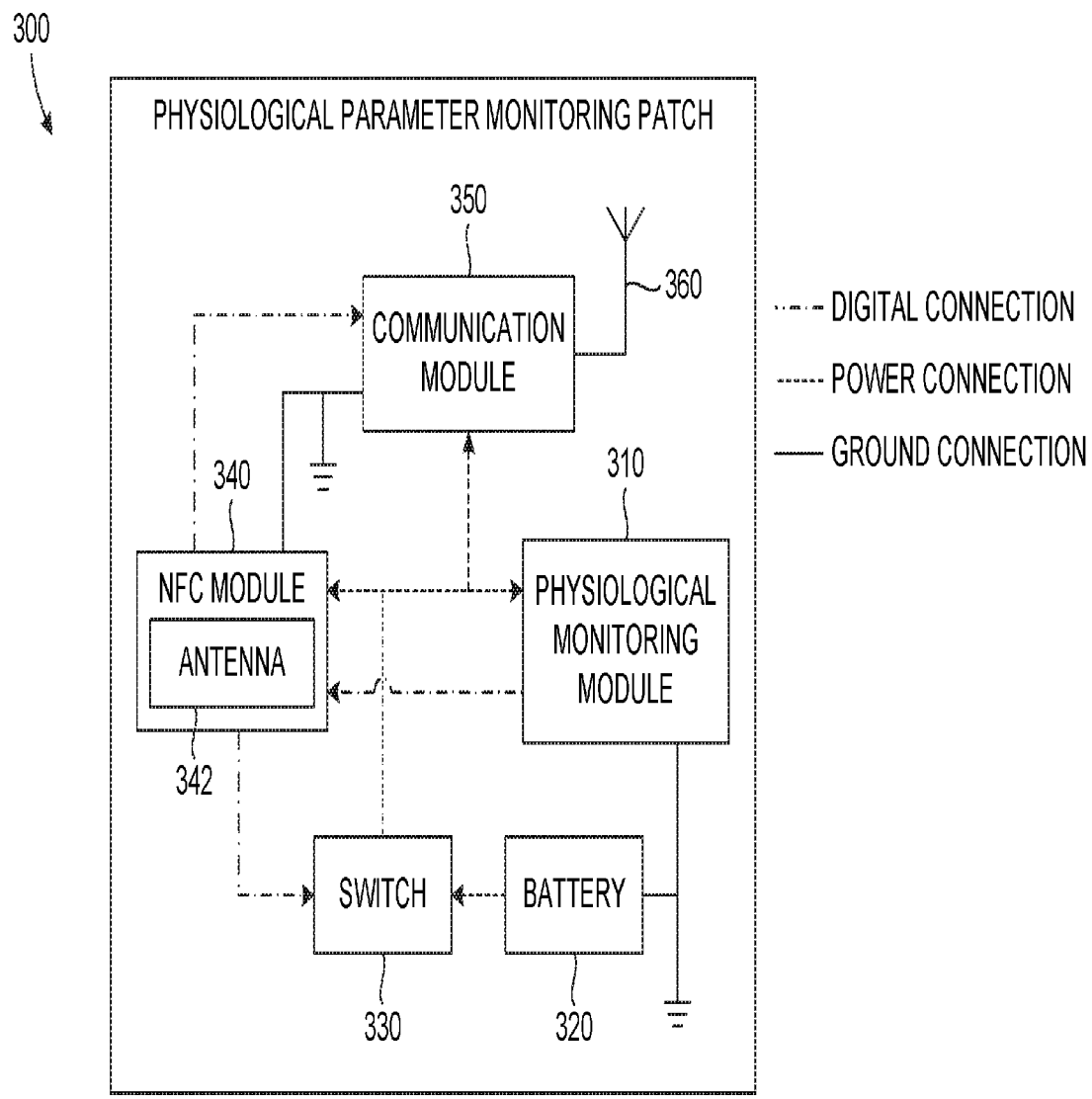
FIG. 3 illustrates an example near-field communication physiological parameter monitoring patch.

FIG. 3 is an example near-field communication (NFC) physiological parameter monitoring patch 300. The NFC patch 300 includes a physiological monitoring module 310, a battery 320, a switch 330, an NFC module 340, a communication module 350 and an antenna 360. Also shown are various pathways/connections, including a digital connection, a power connection and a ground connection. In response to a received NFC signal, the physiological parameter monitoring patch 300 can be activated and can begin to monitor a physiological parameter, sensing data regarding the physiological parameter by the physiological monitoring module 310. The collected physiological data can then be transmitted to an external device/system by the communication module 350 and the antenna 360.

The NFC module 340 includes an antenna 342. The antenna 342 receives an NFC signal from an external device/system, such as a pairing device. The received NFC signal by the antenna 342 induces a current in the NFC module 340, providing power for the NFC module 340 to perform one or more functions. In the example shown in FIG. 3, a controller, processor, or other element, of the NFC module 340 transmits a digital signal to the switch 330. The switch 330, can be a MOSFET element, and can complete one or more circuits in response to the received digital signal from the NFC module 340. Additionally, the NFC module 340 can broadcast a signal in response to the received NFC signal. The response signal can include information to pair the communication module 350 of the physiological parameter monitoring patch 300 with the external device/system to establish a communication channel there between.

The switch 330 can complete a circuit between the battery 320 and the physiological monitoring module 310 and the communication module 350 via the power connection. The physiological monitoring module 310 and/or the communication module 350 can perform one or more functions using power/energy supplied by the battery 320 due to the circuit completed by the switch 330 in response to the received NFC signal by the NFC module. The energized physiological monitoring module 310 can sense and/or collect physiological data regarding one or more physiological parameters by one or more sensors of the physiological monitoring module 310. The collected physiological data can be output as a digital signal that can be transmitted through the NFC module 340 to the communication module 350. The communication module 350 can transmit the collected physiological data to the external device/system via the antenna 360.

The communication module 350 can use one or more communication protocols, such as Wi-Fi, WiGig, and/or Bluetooth®, to transmit the collected physiological data from the physiological parameter monitoring patch 300 to the external device/system. To deactivate the physiological parameter monitoring patch 300, the battery can be decoupled from the other components of the physiological parameter monitoring patch 300 by the switch 330 in response to a signal received by the NFC module 340. The signal received by the NFC module 340 could be a Bluetooth, Wi-Fi, WiGig, or NFC signal, for example, but could include any suitable deactivating signal that instructs the physiological parameter monitoring patch 300 to decouple the battery from the other active components on the patch 300.

In this manner, the physiological parameter monitoring patch 300 can be activated and/or deactivated, as needed or required. The activation/deactivation of the physiological parameter monitoring patch 300 can allow for intermittent monitoring and transmission of physiological data by/from the physiological parameter monitoring patch 300 to the external device/system. Additionally, the activation/deactivation can extend the use time of the physiological parameter monitoring patch 300 due to the intermittent collection/transmission of physiological data, since the use of the physiological parameter monitoring patch 300 is spread out over a longer period of time.

The physiological parameter monitoring patch 300 can be placed on and/or affixed to a patient with one or more securing elements. To secure the physiological parameter monitoring patch 300 to a patient, the physiological parameter monitoring patch 300 can include an adhesive backing, for example, which allows the physiological parameter monitoring patch 300 to be temporarily affixed to the skin of the patient. Alternatively, the physiological parameter monitoring patch 300 can be held against or affixed to the skin of the patient by strapping, taping or bandaging the physiological parameter monitoring patch 300 to the patient.

Figure 4:
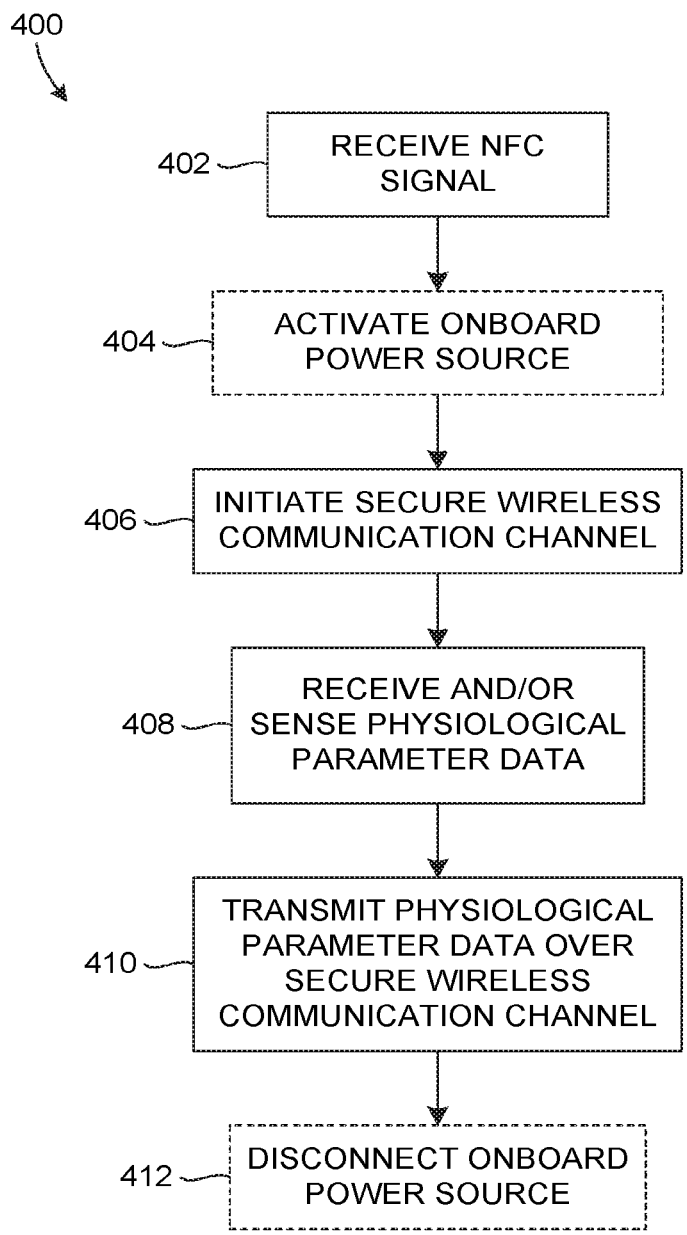
FIG. 4 illustrates an example method of transmitting physiological parameter data from a near-field communication patch.

FIG. 4 is an example method 400 of transmitting physiological data from a near-field communication patch, such as a physiological parameter monitoring patch, to an external device/system. At 402, the physiological parameter monitoring patch receives an NFC signal. In response to the received NFC signal, the physiological parameter monitoring patch can optionally activate an onboard power source at 404. Alternatively, the physiological parameter monitoring patch can derive power from the received NFC signal. At 406, the physiological parameter monitoring patch initiates a secure wireless communication channel with the external device/system. To establish the secure wireless communication channel, the physiological parameter monitoring patch and the external device/system can exchange authentication information, such as a pairing code or more complex security codes such as SHA-1, SHA-2, or SHA-256, for example. Any authentication protocol can be implemented to pair the physiological parameter monitoring patch and the master device. The secure wireless communication channel can be established using one or more communication protocols, such as the Wi-Fi, WiGig, and/or Bluetooth® communication protocol. At 408, the physiological parameter monitoring patch can receive and/or sense physiological parameter data, such as from one or more physiological parameter monitoring sensors. Example physiological parameter monitoring sensors can include sensors to sense a temperature, an electrocardiogram (ECG), a non-invasive blood pressure (NIBP) and/or an oxygen saturation of the patient. The collected physiological data can then be transmitted over the secure wireless communication channel at 410 to the external device/system. At 412, optionally, the onboard power source can be disconnected/deactivated to return the physiological parameter monitoring patch to a dormant state, such as prior to 402.

Figure 5:
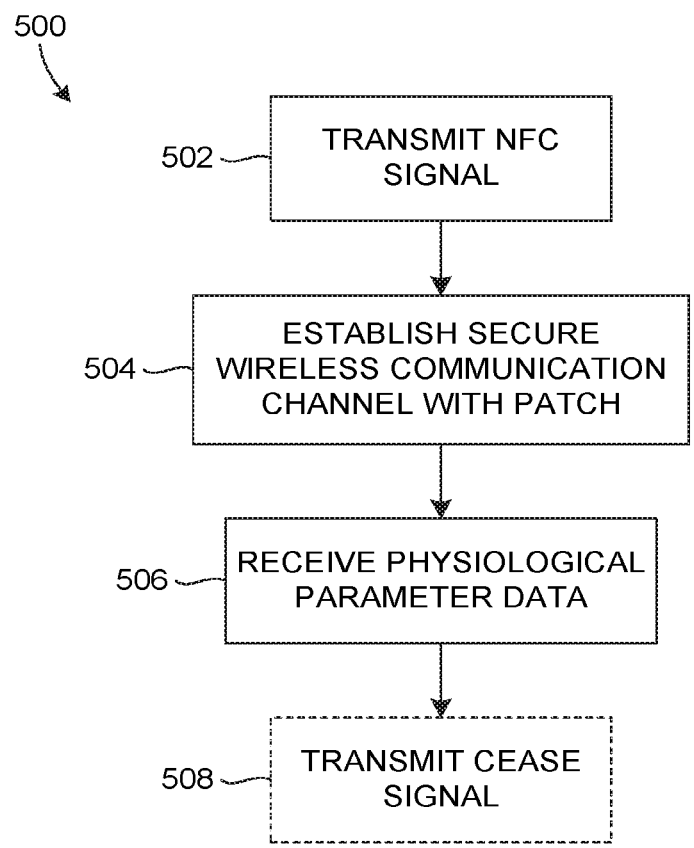
FIG. 5 illustrates an example method of receiving physiological parameter data from a near field communication patch.

FIG. 5 is an example method 500 of receiving physiological data from a near-field communication (NFC) patch, such as a physiological parameter monitoring patch, by an external device/system. At 502, to activate the physiological parameter monitoring patch, the external device/system can transmit an NFC signal. At 504, the external device/system can establish a secure wireless communication channel with the physiological parameter monitoring patch. The secure wireless communication channel can be secured by the exchange of authentication data, such as a pairing code or other authentication protocol, for example, between the external device/system and the physiological parameter monitoring patch. Additionally, the secure wireless communication channel can use one or more communication protocols, such as Wi-Fi, WiGig, and/or Bluetooth®, to transmit and/or receive information via the secure wireless communication channel. At 506, the external device/system can receive physiological parameter data from the physiological parameter monitoring patch. The received physiological parameter data can be collected by one or more sensors of the physiological parameter monitoring patch. At 508, optionally, the external device/system can transmit a cease signal to the physiological parameter monitoring patch. Reception of the cease signal by the physiological parameter monitoring patch can cause the physiological parameter monitoring patch to return to a dormant state, such as prior to 502.

Figure 6:
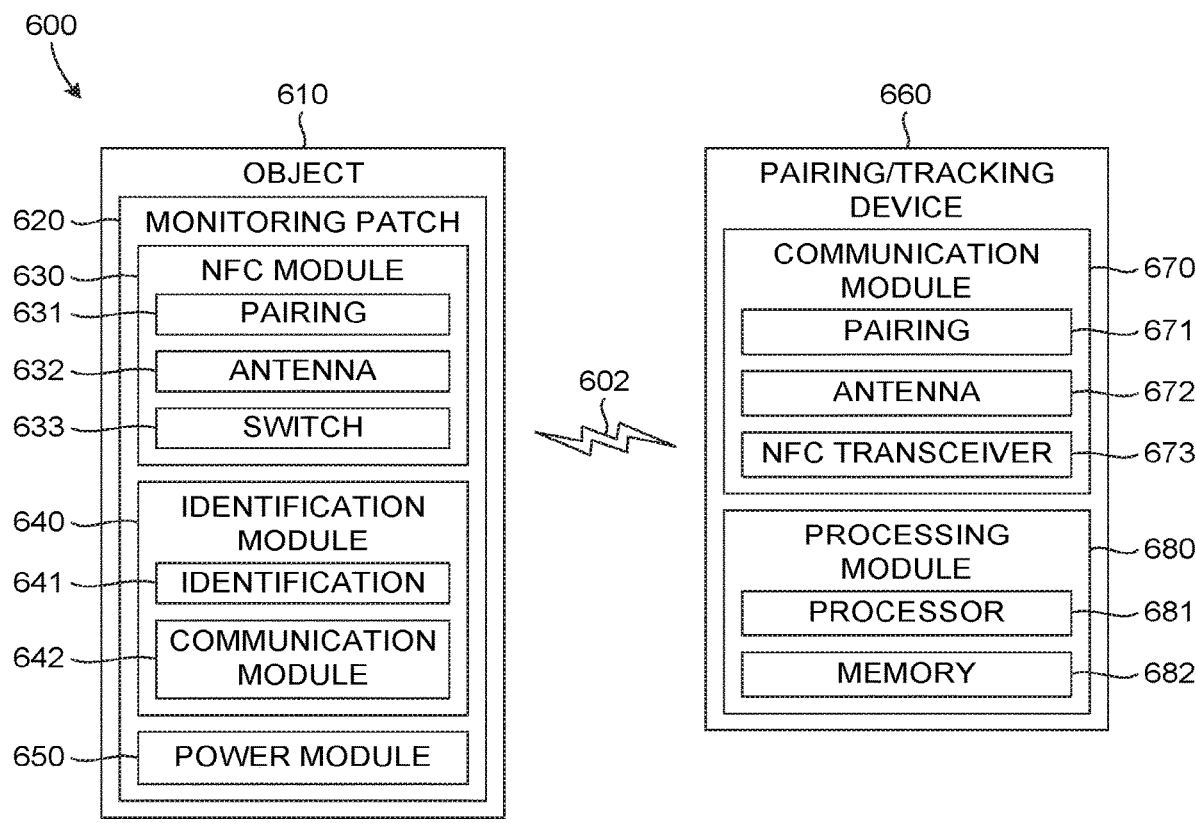
FIG. 6 illustrates a further example block diagram of a near-field communication patch system.

FIG. 6 is a block diagram of a further example near-field communication (NFC) patch system 600 that includes a monitoring patch 620 placed on an object 610 and a pairing/monitoring device 660 that can interrogate the monitoring patch 660 for identification and/or other information. The monitoring patch 620 includes an identification module 640 that includes identification 641 information that identifies and/or includes additional information regarding the object 610. The identification 641 can be communicated by a communication module 642, of the identification module 640, to the pairing/tracking device 660. The pairing/tracking device 660 can receive the identification 641 which can be stored and/or transmitted to an external device, system and/or user, by the pairing/tracking device 660.

The object 610 can be an object that is desired, or required, to be tracked and/or information to be gathered/collected about. For example, the object 610 can include a pill bottle, a patient identification bracelet, an injectable medication and/or other objects. The monitoring patch 620 can include information regarding the object 610 and can transmit the information to the pairing/tracking device 660 when interrogated by the pairing/tracking device 660. This information received by the tracking/pairing device 660 can be used to track the object, such as from an origin to a destination to confirm proper delivery, and/or to confirm the identification of the object, such as confirming the correct injectable medication is being prepared for administration to a patient. Additionally, the tracking can include correlation capabilities, such as allowing confirming two or more objects 610 should be associated together. For example, in preparation to administer a medication, a patient identification can be interrogated to receive patient information that can include data regarding a potential drug interaction and the medication can be interrogated to receive medication information. The tracking capability can confirm that the received patient identification information did not include indications of a drug interaction with the medication that was interrogated. Such tracking can increase patient safety by confirming and/or tracking various information regarding one or more objects 610 by attached monitoring patches 620.

The monitoring patch 620 can include an NFC module 630, the identification module 640 and a power module 650. An NFC signal, such as 602, can be received by the monitoring patch 620 to cause the monitoring patch 620 to be activated and to transmit identification 641 in response to the activation. The NFC module 630 can include an optional pairing 631, an antenna 632 and a switch 633. In response to the received NFC signal 602, a current is induced in the NFC module 630 that can cause the switch 633 to complete a circuit to supply power, or electrical energy, from the power module 650 to the identification module 640, thereby activating the monitoring patch 620. The antenna 632 of the NFC module 630 can receive the NFC signal 602 and can be constructed and/or arranged to have a current induced by the reception of the NFC signal 602. The pairing 631 can include authentication, or other information, that can be transmitted from the monitoring patch 620 to the pairing/tracking device 660 to establish a secured wireless communication channel between the two. Alternatively, an unsecured wireless communication channel between the two can be established. The pairing 631 can include a pairing code/key that can be shared by the monitoring patch 620 and the pairing/tracking device 660 to validate/authenticate the secure wireless communication channel there between.

The identification module 640 can include identification 641 and communication module 642. Once electrically connected to the power module 650 by the switch 633, the communication module 642 can transmit the identification 641 to the pairing/tracking device 660 via the secure wireless communication channel. The secure wireless communication channel can use one or more communication protocols, such as Wi-Fi, WiGig, and/or Bluetooth®.

The identification 641 can include identification of the object 610, such as a patient or medication name, and/or additional object 610 information, such as patient medical information or medication expiration date. The identification 641 can be transmitted by the communication module 642 to the tracking/pairing device 660. The identification 641 can be updated, and/or altered, by received communications/data via the communication module 642. For example, the identification 641 can include object 610 location information. When the monitoring patch 620 is interrogated at a new/different location than that stored in the identification 641, the communication module 642 can request and/or receive updated location information, such as from the pairing/tracking device 660 that can then be stored in the identification 641.

The power module 650 can include one or more energy storage devices, such as a battery, that can be permanent or replaceable. The power module 650 can be disconnected and/or connected from one or more components of the monitoring patch 620 by the switch 633 in response to a received NFC signal 602. Additionally, the identification module 640 can cause the switch 633 to disconnect the power module 650 once the transmission of the identification 641 is complete. This can allow the monitoring patch 620, and in some examples the object 610, to preserve power by disconnecting the power module 650 to prevent depletion of the power module 650 while the monitoring patch 620 is in a dormant state.

The pairing/tracking device 660 can include a communication module 670 and a processing module 680. The pairing/tracking device 660 can emit the NFC signal 602 to activate the monitoring patch 620 on the object 610 to receive object 610 identification 641, and/or other object 610 information, from the monitoring patch 620. The collected object 610 identification 641 and/or other information can be stored, such as in memory 682, provided to a user, such as by a visual and/or audible output, and/or transmitted to an external device/system, such as by the communication module 670.

The communication module 670 can include pairing 671, an antenna 672 and an NFC transceiver 673. The NFC transceiver 673 can emit the NFC signal 602 and can receive a response signal from the NFC module 630 of the monitoring patch 620. The response signal can include pairing 631 that can be stored as pairing 671 of the communication module 670. In this manner, the pairing 631 of the monitoring patch 620 is synchronized to/matched with the pairing 671 of the pairing/tracking device 660. Alternatively, the pairing 671 of the pairing/tracking device 660 can be transmitted to the monitoring patch 620, to be stored as pairing 631, by the NFC transceiver 673 emitted NFC signal 602. The sharing of the pairing 631, 671 between the monitoring patch 620 and the pairing/tracking device 660 can allow the secure wireless communication channel there between to be established, secured and/or authenticated.

The antenna 672 can receive identification 641 from the monitoring patch 620 in an active state and/or can transmit data to the monitoring patch 620 via the secure wireless communication channel. The antenna 672 can also communicate with an external device/system via a wireless communication channel that can be secured or unsecured. Identification 641, or other data, can be transmitted to the external device/system via the antenna 672.

The processing module 680 can include a processor 681 and memory 682. The processor 681 can process information, execute instructions, such as stored in the memory 682, and/or can control one or more functions/features of the pairing/tracking device 660. The memory 682 can store received identification 641 and the processor 681 can optionally correlate/analyze received identification 641 information from one or more objects 610. The correlation/analysis of the received identification 641 information can be used to determine potential relationship issues between the one or more objects 610, such as a drug interaction and/or a wrongful administration of a medication.

Figure 7:
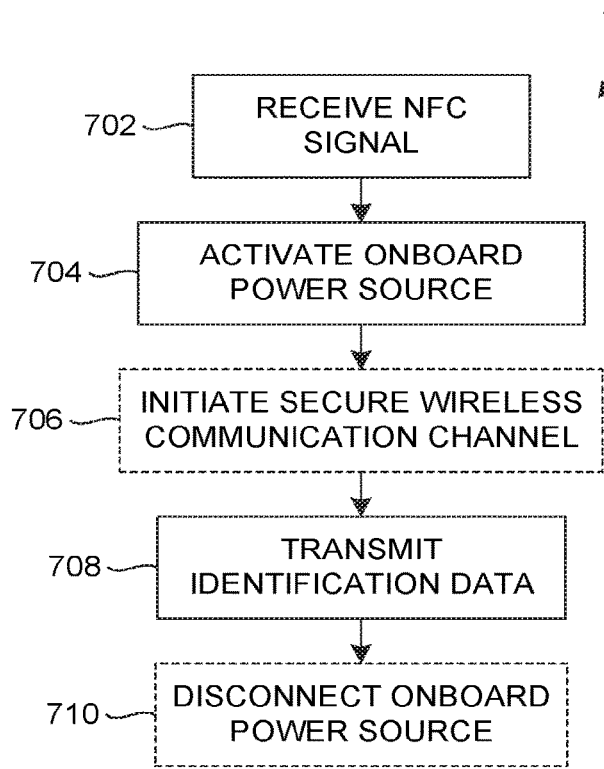
FIG. 7 illustrates an example method of transmitting identification data from a near-field communication patch.

FIG. 7 is an example method 700 of transmitting identification data from a monitoring patch. At 702, the monitoring patch receives an NFC signal. The received NFC signal causes an onboard power source to be activated at 704. In an example, the NFC signal received at 702 can induce a current in the monitoring patch that can cause a switch to electrically couple one or more components/systems of the monitoring patch to the onboard power source, such as a battery. At 706, a secure wireless communication channel can be optionally initiated. The secure wireless communication channel can be established between the monitoring patch and an external device/system, such as the external device/system that transmitted the NFC signal at 702. Alternatively, an unsecured wireless communication channel can be established. At 708, identification information is transmitted. The identification information can include an identification of an object upon which the monitoring patch is placed or affixed, and/or can include other information regarding the object. At 710, the onboard power source can be optionally disconnected. The disconnection of the onboard power source from the one or more components/systems of the monitoring patch can be in response to a received signal from the external device/system, can be a timer based disconnect and/or can be in response to the transmission of the identification data at 708.

Figure 8:
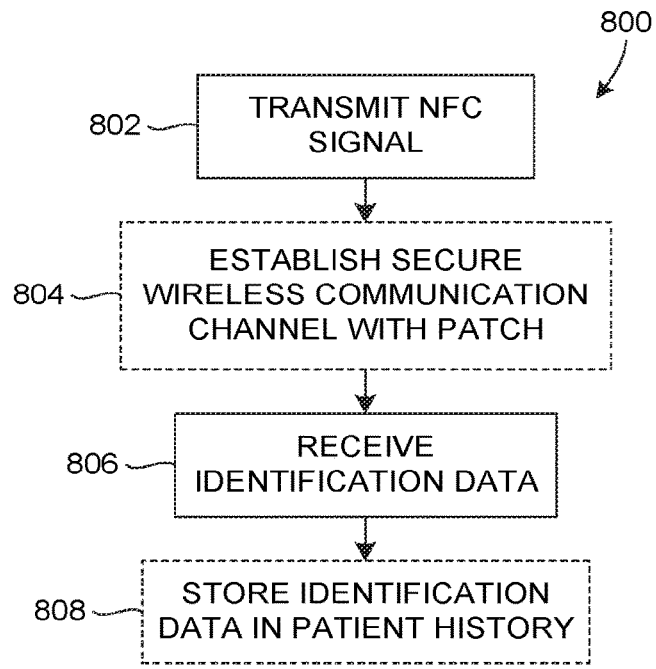
FIG. 8 illustrates an example method of receiving identification data from a near-field communication patch.

FIG. 8 is an example method 800 for receiving identification information, such as by an external device/system from a monitoring patch on an object. At 802, an NFC signal can be transmitted. The transmitted NFC signal, such as from the external device/system, can cause the monitoring patch to transition from a dormant state to an active state in which an onboard power source is electrically coupled to one or more components/systems of the monitoring patch. At 804, an optional secure wireless communication channel can be established with the monitoring patch. An exchange of pairing codes/keys can be used to establish the secure wireless communication channel between the external device/system and the monitoring patch. Alternatively, the wireless communication channel can be unsecured. At 806, identification data is received, such as receiving identification and/or other object data from the monitoring patch. At 808, the received identification data can be optionally stored in a patient history. The storing of the identification and/or other object data in the patient history can track the use of one or more objects with relation to a particular patient.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A wearable device, comprising:
  a memory;
  a sensor configured to detect a physiological parameter of a patient and to generate data representing the physiological parameter;
  a display configured to present a current time when the wearable device is in a time state;
  a processor configured to:
    in response to periodically checking a sensed parameter and identifying the sensed parameter exceeds a first threshold, transition the wearable device from operating in the time state for presenting, by the display, the current time to a monitor state for monitoring the data representing the physiological parameter;
    receive the data generated by the sensor in response to the wearable device transitioning from operating in the time state to the monitor state;
    cause the data to be stored in the memory;
    when the wearable device operates in the monitor state, analyze the data; and
    in response to receiving a signal with a schedule instructing when the wearable device is to transmit the data, and to determining that the physiological parameter exceeds a second threshold, transition the wearable device from operating in the monitor state to a transmit state for transmitting the data; and
  a transceiver configured to transmit the data in response to the wearable device transitioning from operating in the monitor state to the transmit state.

2. The wearable device of claim 1, further comprising:
  a battery; and
  a switch configured to electrically connect the battery to the sensor when the wearable device transitions to operating in the monitor state.

3. The wearable device of claim 1, wherein the processor is configured to:
  in response to:
    receiving an initial signal with an initial schedule instructing when the wearable device is to monitor the data,
    periodically checking the sensed parameter, determining that the sensed parameter exceeds the first threshold, and
    determining that a current time exceeds a preset time that triggers monitoring of the data,
  transition the wearable device from operating in the time state to the monitor state.

4. The wearable device of claim 1, wherein the processor is configured to:
  in response to:
    receiving an initial signal with a schedule instructing when the wearable device is to monitor the data,
    periodically checking the sensed parameter, and
    determining that the sensed parameter exceeds the first threshold, transition the wearable device from operating in the time state to the monitor state; and
  in response to:
    receiving the signal with the schedule instructing when the wearable device is to transmit the data, identifying the physiological parameter exceeds the second threshold, and identifying the current time exceeds a preset time that triggers the transmitting of the data, transition the wearable device from operating in the monitor state to the transmit state.

5. A wearable device, comprising:

a memory;

a sensor configured to detect a physiological parameter of a patient and to generate data representing the physiological parameter;

a display configured to present a current time when the wearable device is in a first state;

a processor configured to:
   in response to periodically checking a sensed parameter and to determining that the sensed parameter exceeds a first threshold, transition the wearable device from operating in the first state to a second state;
   receive the data when the wearable device transitions from operating in the first state to the second state;
   cause the data to be stored in the memory;
   when the wearable device operates in the second state, analyze the data; and
   in response to receiving a signal instructing when the wearable device is to transmit the data, and to determining that the physiological parameter exceeds a second threshold, transition the wearable device from operating in the second state to a third state; and a transceiver configured to, in response to the wearable device transitioning from operating in the second state to the third state, transmit the data.

6. The wearable device of claim 5, wherein the first state comprises a time state during which a portion of the wearable device is dormant, and
   wherein the second state comprises a monitor state.

7. The wearable device of claim 5, wherein the second state comprises a monitor state, and the third state comprises a transmit state.

8. The wearable device of claim 5, further comprising:
a circuit;
a power source; and
a switch,
   wherein the processor is further configured to:
      receive the data continuously; and
      in response to receiving a signal, cause the switch to connect the power source to the circuit.

9. The wearable device of claim 5, wherein the processor is configured to receive the data by, in response to receiving a signal or user input, receiving the data continuously.

10. The wearable device of claim 5, wherein the processor is configured to receive the data by, in response to receiving signals at intervals, receiving the data intermittently.

11. The wearable device of claim 5, wherein the processor is configured to cease analyzing the data in response to the wearable device transitioning to operating in the third state.

12. The wearable device of claim 5, further comprising:
a battery; and
a circuit configured to draw less power from the battery when the wearable device is operating in the first state than when the wearable device is operating in the second state.

13. The wearable device of claim 5, further comprising:
a battery; and
a circuit configured to draw less power from the battery when the wearable device is operating in the second state than when the wearable device is operating in the third state.

14. A method, comprising:

detecting, by a sensor of a wearable device, a physiological parameter of a patient;

generating, by the sensor, data representing the physiological parameter;

selectively presenting, by a display, a current time when the wearable device is in a first state;

in response to periodically checking a sensed parameter and to determining that the sensed parameter exceeds a first threshold, transitioning the wearable device from operating in the first state to a second state;

receiving, by a processor of the wearable device, the data when the wearable device transitions from operating in the first state to the second state;

when the wearable device operates in the second state, analyzing the data;

in response to receiving a signal instructing when the wearable device is to transmit the data, and to determining that the physiological parameter exceeds a second threshold, transitioning the wearable device from operating in the second state to a third state; and in response to the wearable device transitioning from operating in the second state to the third state, transmitting the data.

15. The method of claim 14, further comprising:

electrically connecting, by a switch of the wearable device, a battery of the wearable device to the sensor when the wearable device transitions to operating in the second state.

16. The method of claim 14, wherein:

receiving the data further comprises receiving the data when the wearable device transitions from operating in a time state as the first state to a monitor state as the second state; and a portion of the wearable device is dormant when the wearable device is operating in the time state.

17. The method of claim 14, wherein transmitting the data further comprises, in response to the wearable device transitioning from operating in a monitor state as the second state to a transmit state as the third state, transmitting the data.

18. The method of claim 14, wherein a circuit of the wearable device operating in the first state draws less power from a battery than in the second state.

19. The method of claim 14, wherein a circuit of the wearable device operating in the second state draws less power from a battery than in the third state.

20. The method of claim 14, wherein receiving the data further comprises:

operating the wearable device in a time state as the first state in response to receiving, by a transceiver of the wearable device, a signal that activates the wearable device; and receiving, by the processor, the data when the wearable device transitions from operating in the time state to a monitor state as the second state.

* * * * *